US010660862B2

(12) United States Patent
Sapkal et al.

(10) Patent No.: US 10,660,862 B2
(45) Date of Patent: May 26, 2020

(54) PHARMACEUTICAL MICROEMULSION IMMOBILIZED IN A THIN POLYMER MATRIX AND METHODS OF MAKING THEM

(71) Applicant: ZIM LABORATORIES LIMITED, Kalmeshwar, Maharashtra (IN)

(72) Inventors: Prakash Sapkal, Kalmeshwar (IN); Nidhi Sapkal, Kalmeshwar (IN); Varsha Pokharkar, Kalmeshwar (IN); Lubna Daud, Kalmeshwar (IN)

(73) Assignee: ZIM LABORATORIES LIMITED, Kalmeshwar (IN)

( * ) Notice: Subject to any disclaimer, the term of this patent is extended or adjusted under 35 U.S.C. 154(b) by 0 days.

(21) Appl. No.: 15/105,802

(22) PCT Filed: Dec. 16, 2014

(86) PCT No.: PCT/IN2014/000779
§ 371 (c)(1),
(2) Date: Jun. 17, 2016

(87) PCT Pub. No.: WO2015/107544
PCT Pub. Date: Jul. 23, 2015

(65) Prior Publication Data
US 2016/0317462 A1 Nov. 3, 2016

(30) Foreign Application Priority Data
Dec. 17, 2013 (IN) .......................... 3947/MUM/2013

(51) Int. Cl.
| | |
|---|---|
| *A61K 9/70* | (2006.01) |
| *A61K 38/28* | (2006.01) |
| *A61K 9/107* | (2006.01) |
| *A61K 9/113* | (2006.01) |
| *A61K 38/23* | (2006.01) |
| *A61K 38/18* | (2006.01) |
| *A61K 38/26* | (2006.01) |
| *A61K 38/22* | (2006.01) |
| *A61K 38/29* | (2006.01) |
| *A61K 38/31* | (2006.01) |
| *A61K 31/444* | (2006.01) |
| *A61K 31/496* | (2006.01) |
| *A61K 31/5415* | (2006.01) |
| *A61K 31/196* | (2006.01) |
| *A61K 31/403* | (2006.01) |
| *A61K 31/216* | (2006.01) |

(Continued)

(52) U.S. Cl.
CPC ............ *A61K 9/7007* (2013.01); *A61K 9/006* (2013.01); *A61K 9/1075* (2013.01); *A61K 9/113* (2013.01); *A61K 31/196* (2013.01); *A61K 31/216* (2013.01); *A61K 31/403* (2013.01); *A61K 31/436* (2013.01); *A61K 31/437* (2013.01); *A61K 31/444* (2013.01); *A61K 31/445* (2013.01); *A61K 31/4515* (2013.01); *A61K 31/496* (2013.01); *A61K 31/5415* (2013.01); *A61K 31/64* (2013.01); *A61K 38/1816* (2013.01); *A61K 38/2264* (2013.01); *A61K 38/23* (2013.01); *A61K 38/26* (2013.01); *A61K 38/28* (2013.01); *A61K 38/29* (2013.01); *A61K 38/31* (2013.01); *A61K 47/10* (2013.01); *A61K 47/12* (2013.01); *A61K 47/26* (2013.01); *A61K 47/32* (2013.01); *A61K 47/34* (2013.01); *A61K 47/38* (2013.01)

(58) Field of Classification Search
None
See application file for complete search history.

(56) References Cited

U.S. PATENT DOCUMENTS

| 6,306,434 B1 | 10/2001 | Hong et al. | |
|---|---|---|---|
| 2004/0151774 A1* | 8/2004 | Pauletti ................ | A61K 9/0034 424/486 |

(Continued)

FOREIGN PATENT DOCUMENTS

| WO | 2003/013421 A2 | 2/2003 |
|---|---|---|
| WO | 2003/051334 A2 | 6/2003 |

(Continued)

OTHER PUBLICATIONS

S Gibaud, D Attivi. "Microemulsions for oral administration and their therapeutic applications." Expert Opinion in Drug Delivery, vol. 9(8), 2012, pp. 937-951. (Year: 2012).*
S Shafiq, F Shakeel, S Talegaonkar, FJ Ahmad, RK Khar, M Ali. "Development and bioavailability assessment of ramipril nanoemulsion formulation." European Journal of Pharmaceutics and Biopharmaceutics, vol. 66, 2007, pp. 227-243. (Year: 2007).*
A Cilek, N Celebi, F Timaksiz. "Lecithin-Based Microemulsion of a Peptide for Oral Administration: Preparation, Characterization, and Physical Stability of the Formulation." Drug Delivery, vol. 13, 2006, pp. 19-24. (Year: 2006).*

(Continued)

*Primary Examiner* — Isaac Shomer
(74) *Attorney, Agent, or Firm* — Maschoff Brennan

(57) ABSTRACT

The invention comprises a ready to use film dosage form comprising microemulsion of an Active Pharmaceutical Ingredient embedded or immobilized in a thin polymeric matrix as a double microemulsion and a process of making the same. The microemulsion in the film dosage form of this invention is capable of being absorbed through mucosal route. The process of making the film dosage of this invention comprises steps of forming a film forming dispersion containing film forming polymers, excipients and microemulsion of active pharmaceutical ingredient, casting the same in the form of a film and drying the cast of the film being carried out by means of drying conditions that suit to retain stability of the active pharmaceutical ingredient being selected such that drying of the film is achieved retaining the moisture trapped in the microemulsion embedded in the polymeric film.

19 Claims, No Drawings

(51) Int. Cl.
  *A61K 31/64*       (2006.01)
  *A61K 31/445*      (2006.01)
  *A61K 9/00*        (2006.01)
  *A61K 31/4515*     (2006.01)
  *A61K 31/437*      (2006.01)
  *A61K 31/436*      (2006.01)
  *A61K 47/10*       (2017.01)
  *A61K 47/12*       (2006.01)
  *A61K 47/26*       (2006.01)
  *A61K 47/32*       (2006.01)
  *A61K 47/34*       (2017.01)
  *A61K 47/38*       (2006.01)

(56) References Cited

U.S. PATENT DOCUMENTS

| | | | |
|---|---|---|---|
| 2009/0047350 A1 | 2/2009 | Bangalore | |
| 2010/0221309 A1* | 9/2010 | Myers | A61K 8/0208 424/443 |
| 2011/0305768 A1* | 12/2011 | Mao | A61K 39/15 424/499 |
| 2013/0309294 A1* | 11/2013 | Rubin | A61K 9/006 424/443 |

FOREIGN PATENT DOCUMENTS

| | | |
|---|---|---|
| WO | 2004/041118 A2 | 5/2004 |
| WO | 2007/067494 A1 | 6/2007 |
| WO | 2011/143424 A1 | 11/2011 |
| WO | 2012/104834 A1 | 8/2012 |
| WO | 2013/026002 A1 | 2/2013 |
| WO | WO-2015083181 A2 * | 6/2015 |

OTHER PUBLICATIONS

W Abdelwahed, G Degobert, S Stainmesse, H Fessi. "Freeze-drying of nanoparticles: Formulation, process and storage considerations." Advanced Drug Delivery Reviews, vol. 58, 2006, pp. 1688-1713. (Year: 2006).*

X Wu, Y Liu, X Li, P Wen, Y Zhang, Y Long, X Wang, Y Guo, F Xing, J Gao. "Preparation of aligned porous gelatin scaffolds by unidirectional freeze-drying method." Acta Biomaterialia, vol. 6, 2010, pp. 1167-1177. (Year: 2010).*

SM Trey, DA Wicks, PK Mididoddi, MA Repka. "Delivery of Itraconazole from Extruded HPC Films." Drug Development and Industrial Pharmacy, vol. 33, 2007, pp. 727-735. (Year: 2007).*

W Kriangkrai, S Puttipipatkhachorn, p. Sriamornsak, T Pongjanyakul, and S Sungthongjeen. "Impact of Anti-tacking Agents on Properties of Gas-Entrapped Membrane and Effervescent Floating Tablets." AAPS PharmSciTech, vol. 15 No. 6, Dec. 2014, pp. 1357-1369. (Year: 2014).*

Moreno et al., "Lyophilized Lecithin Based Oil-Water Microemulsions as a New and Low Toxic Delivery System for Amphotericin B." Pharmaceutical Research vol. 18, Issue 3, Mar. 2001: pp. 344-351.

* cited by examiner

PHARMACEUTICAL MICROEMULSION IMMOBILIZED IN A THIN POLYMER MATRIX AND METHODS OF MAKING THEM

FIELD OF THE INVENTION

The invention pertains to stable microemulsions immobilized in a thin polymer matrix compositions and a process of making the same. In particular, the invention pertains to stable pharmaceutical microemulsion by immobilization in polymer matrix.

BACKGROUND OF THE INVENTION

Microemulsions are used as vehicles for drug delivery. This system can be used by various routes like topical, oral, buccal, sublingual, nasal, vaginal, rectal and intravenous. Advantages of microemulsions are as follows:
  These are formed spontaneously on mixing all the components.
  Penetration of water soluble drugs is enhanced using water-in-oil microemulsion.
  Solubility of lipophilic drugs is enhanced when used as oil-in-water microemulsion.
  Release rate of drugs can be controlled.
  Molecules can be protected from hydrolysis and oxidation.
  Taste masking can be achieved.

Along with these advantages there are some serious limitations of this drug delivery system. Being fluid in nature, maintaining dose uniformity, handling and transportation are difficult to manage in microemulsions. Although presence of surfactants and co-surfactants impart sufficient stability to this dispersed system, it is affected by environmental conditions like pH, temperature etc.

Hence, to make microemulsions useable for therapeutic purpose, it is necessary to make a drug delivery system from such microemulsions which have dose uniformity, convenience in handling, storage stability and suitability to different routes of administration.

In practical terms, a solid dosage form is preferable to a liquid dosage form in respect of convenience, ease of handling and accurate dosing. Hence, attempts have been made to encapsulate microemulsions in soft gelatine capsules. However, limitation with this kind of delivery is that it can be used only for oral route and not for any other route of administration The dispersed systems in the form of liquids are more prone to instability and excipient incompatibility. Many researchers have attempted to develop powder, re-dispersible emulsion-derived formulations known as dry emulsion from these fluid microemulsions by removing water from water in oil microemulsion, using water soluble or insoluble carriers, by rotary evaporation, lyophilisation or spray drying. However, all of them have some or the other drawback. Common drawback is that the resulting loss of water results in loss of activity of some Active Pharmaceutical Ingredients. This includes, for example, without limitation, macromolecules, particularly enzymes which are sensitive to changes in pH, loss of water, loss of three dimensional structure. This also includes, without limitation, thermolabile Active Pharmaceutical Ingredients, for example, Ketorolac tromethamine, Doxylamine succinate, tetracycline, misoprostol, methylcobalamine, Cholecalciferol, serratiopeptidase, etc.

Moreno et al (Pharmaceutical Research 2001; 18(3):344-351) lyophilized an amphotericin B containing lecithin based o/w microemulsion. But the final formulation was an oily cake and was intended to be used after reconstitution in water. The reconstitution involved addition of measured quantity of water and stirring using magnetic stirrer. After this processing microemulsions were obtained.

So, the work was done to reduce fluidity of microemulsions and not to convert fluid dosage form to solid dosage form while retaining microemulsion properties.

Remidia et al (WO2003051334A2) disclosed a pharmaceutical composition comprising a poorly soluble drug, in powder or microgranular form, comprising an oil/water/oil double microemulsion incorporated into a solid support constituted by a microporous inorganic substance or by an adsorbent colloidal inorganic substance or by a cross-linked swellable in water polymer, wherein said drug is dissolved or dispersed in one or more of the phases of said microemulsion. The composition according to claim 1, formulated with pharmaceutically acceptable excipients or diluents, for use in capsules, pills, sachets and suspensions by incorporation of the o/w/o microemulsion of stage d) into a support in the form of a powder by slowly adding said microemulsion to said support in powder form, maintaining said support under constant mixing/agitation in an equipment selected from high efficiency of mixing granulators, extruders and fluid bed granulators. The solid microporous carrier included, cross linked PVP, silica, silicates, zeolytes, alumina, activated carbon, colloidal silica, magnesium trisilicate, argil, magnesium oxide, talc, CMC starch, CMC cellulose, polystyrene, polymethylmethacrylate etc.

Hong et al (U.S. Pat. No. 6,306,434) disclose a cyclosporin solid-state microemulsion comprising a solidified product consisting essentially of a cyclosporin microemulsion dispersed in an enteric carrier. The enteric polymer containing material was one or more chosen from the group consisting of aqueous methacrylic polymers, hydroxypropyl methylcellulose phthalates, cellulose acetate phthalate and sodium alginate. Here, cyclosporin microemulsion is added to the solution of the enteric carrier, and mixed to make it homogeneous. The solution was then evaporated slowly at low temperature under reduced pressure to remove the solvent completely. Cyclosporin solid-state microemulsion film produced was powdered, and formulated into pharmaceutical preparations, that is, capsule, powder, granule and tablet according to conventional methods. The intermediate product is obtained as film, which was powdered, and formulated using conventional methods into the final pharmaceutical dosage form that is other than a film comprising, without limitations, capsule, powder, granule and tablet. Moreover in this work instead of liquid state microemulsion, a "cyclosporin solid-state microemulsion" i.e. a "solidified product of microemulsion pre-concentrate containing cyclosporin" is used in the sense that they can form microemulsion spontaneously after being dissolved in such external phases as water, etc. Thus, the products of Hong et al do not contain a microemulsion in its liquid form/state.

Retaining compatible solvent at proper pH and other conditions in the microemulsion is needed to retains stability and activity of several pharmaceutical actives, including but not limited to, peptides and enzymes. Hence, a drug delivery system is needed wherein it is a solid dosage form but micro-emulation ingredient in it is not in a dehydrated solid form.

SUMMARY OF INVENTION

The invention comprises a ready to use film dosage form comprising microemulsion of an Active Pharmaceutical Ingredient. In one embodiment the film dosage form of this invention contains microemulsion embedded or immobilized in a thin polymeric matrix that is water soluble. In a further aspect of this invention, embedding/immobilizaiton of the microemulsion is done in its original state without removal of water contained in the micro-emulsion. The original state of microemulsion is a liquid state. In a still further aspect, the micro-emulsion is embedded in the film as a double microemulsion.

The ready to use film dosage form of this invention has moisture content which is at least equal to the moisture bound in the emulsion component. The micro-emulsion of the Active Pharmaceutical Ingredient in the film dosage form of this invention is capable of being absorbed through mucosal route and is added in a therapeutically effective quantity. The film dosage form according to claim 1 containing microemulsion, wherein the microemulsion is a water-in-oil (w/o) microemulsion, a oil-in-water emulsion.

In a further embodiment, the oil-in-water micro-emulsion incorporated in the film dosage form of this invention is made of a poorly water soluble active ingredient added in a therapeutically effective quantity.

In one embodiment, the film dosage form of this invention comprises one or more of features selected from the group consisting of foldable, flexible, non-tacky, fast dissolving or fast dispersing, bioadhesive and enabling mucosal administration of drugs. The said mucosal route comprises one or more selected from the group buccal, sublingual, nasal, rectal and vaginal route.

In another embodiment of this invention, the film dosage form of this invention produces micro-emulsion upon dissolution/dispersion the film.

In yet another embodiment, the film dosage form of this invention is fast dissolving and consumable orally without the need for water.

This invention also comprises a process of making ready to use film dosage form comprising microemulsion of a therapeutically active ingredient immobilized in a thin polymeric matrix comprising steps of forming a film forming dispersion containing film forming polymers, excipients and microemulsion of active pharmaceutical ingredient, casting the same in the form of a film and drying of the cast of the film being carried out by means of drying conditions that suit to retain stability of the active pharmaceutical ingredient. In one embodiment, the drying conditions are selected that achieves drying of the film retaining the moisture trapped in the microemulsion embedded in the polymeric film. The drying conditions that achieves drying of the film retaining the moisture trapped in the microemulsion embedded in the polymeric film are selected, without limitation, from the group consisting of (a) use of mild heat for thermostable drugs, and (b) carrying out (i) film casting and drying without the need of heat, or (ii) freeze drying for thermolabile drugs. In the process of this invention, the microemulsion is incorporated in liquid state within a range of from a trace quantity to up to 49% of the mass of the film. In the process of this invention, the micro-emulsion in the film forming emulsion may stabilized by the gels formed upon removal of water during drying.

DETAILED DESCRIPTION OF INVENTION

For the purpose of this specification, microemulsions are defined as a thermodynamically stable, fluid, transparent dispersion of oil and water stabilized by an interfacial film of amphiphillic molecules known as surfactants. Microemulsion may be "oil-dispersed in-water" or "water dispersed-in-oil".

This invention comprises a ready to use film dosage form comprising microemulsion of Active Pharmaceutical Ingredients. In one aspect, the film dosage forms of this invention comprise microemulsion of Active Pharmaceutical Ingredients immobilized in thin polymeric matrix. In a further aspect of this invention, the film dosage forms of this invention comprise microemulsion of Active Pharmaceutical Ingredients immobilized by embedding in thin polymeric matrix. In a still further aspect of this invention, the film dosage forms of this invention comprise microemulsion of Active Pharmaceutical Ingredients immobilized by embedding in thin polymeric matrix wherein they contain moisture that is equal to the moisture contained in the microemulsion before adding the same to the film forming emulsion. The fact that micro-emulsions retain their liquid form in the film is evident from the observation that when a film that does not contain microemulsion is dissolved in water, it dissolves completely without leaving behind any particles suspensed in water; whereas when a film that contains microemulsion embedded/immobilized in it is dissolved in water, the microemulsion is detected in the water in colloidal form. Another evidence also comes from the observation that sublingual film of this invention containing insulin was seen to lower blood sugar, which is not possible unless the microemulsion remains in its original form in the film after making the film. Usually, due to water content of the micro-emulsion, the films containing microemutsion in embedded/immobilized form contain additional moisture content that corresponds to the water content of the micro-emulsion immobilized therein. Thus, this invention comprises a pharmaceutical microemulsion in its liquid form immobilized in a thin polymeric matrix of a ready to use film dosage form. In this embodiment, this invention comprises a product which exhibits advantages of both, film and microemulsion. It is an embodiment of this invention that the films of this invention are water soluble, which are also perceived to have same meaning, for the purpose of this invention, as water dissolvable or water dispersible.

In one embodiment the resulting films are foldable, flexible, non-tacky, fast dissolving and upon the dissolution/dispersion produces microemulsion.

In another embodiment of this invention, this film dosage form incorporating microemulsion added in liquid state and further stabilized, can be cut into desired size containing an accurate amount of dose per piece. This makes accurate delivery of dosage convenient.

In a further embodiment, the film dosage form incorporating microemulsion is bioadhesive, enabling buccal, sublingual, nasal, rectal, vaginal routes of administration of drugs.

In another embodiment, the film dosage form incorporating microemulsion comprises a water-in-oil (w/o) microemulsion. In this embodiment, the drugs that may be incorporated in the microemulsion includes, without limitations, insulin, teriperatide, calcitonin, glucagon, somatostatin, leptin, erythropoietin, etc. In another embodiment, vaccines capable of being absorbed through mucosal route are incorporated in the orally dissolving thin film dosage form incorporating Microemulsion. These are the drugs that are not absorbed through gastro-intestinal tract since they degrade when ingested. Addition of macromolecule penetration/absorption enhancers, such as, including but not limited to in topical, transdermal, transmucosal dosage forms such as creams, patches, suppositories etc. is common; and addition of the same may also be done in the film dosage forms of this invention.

In another embodiment, the film dosage form incorporating microemulsion in liquid state comprises a oil in water (o/w) microemulsion. In this embodiment, the drugs that may be incorporated in the microemulsion includes, without limitation, poorly water soluble drugs like Haloperidol, meloxicam, etoricoxib, fenofibrate, itraconazole, tacrolimus, cyclosporine A, zolpidem etc.

In a further embodiment, the microemulsion incorporated in the film dosage form of this invention comprises a pharmaceutical Active/drug in therapeutically effective quantity.

In still another embodiment of the film dosage form incorporating microemulsion in liquid state comprises incorporation of the microemulsion from a trace quantity to up to 49% of the mass of the film.

This invention also comprises a process of making a film dosage form incorporating microemulsion in liquid state wherein drying of final film forming dispersion is done by using means that suit to retain stability of the pharmaceutical active/drug. Thus, in one further embodiment, mild heat is used for thermostable drugs, and freeze drying is used for thermolabile drugs. In a further embodiment, for incorporating thermolabile drugs, film casting and drying is done without the need of heat.

This invention also comprises a process of making a film dosage form incorporating microemulsion in liquid state of w/o (water-in-oil) wherein the process comprises a step of preparing a double emulsion, w/o/w (water-in-oil-in-water) of microemulsion in the film forming dispersion. Without getting bound to any theory, it is considered that the double emulsion is considered as providing stability to the product.

This invention also comprises a process of making a film dosage form incorporating microemulsion in liquid state of o/w type (Oil-in-Water type) wherein the process comprises a step of gelating/gelling the microemulsion in the film forming dispersion. Without getting bound to any theory, it is considered that gelating/gelling the microemulsion is considered as providing stability to the product. In one embodiment of this invention, HPMC used as film forming agent acts as gelating/gelling agent.

In one embodiment of this invention the thin film dosage form incorporating microemulsion can be made orally dissolving and can be consumed orally without the need for water.

In another embodiment, the film dosage form incorporating microemulsion in liquid state enables administration of macromolecules that degrade in gastrointestinal tract is done using other routes through mucous membrane. The other routes enabling administration through mucous membrane includes, without limitations, sublingual, buccal, nasal, vaginal, rectal routes etc.

Without getting bound to the theory, it is contemplated that process steps followed for making the films of this invention achieve stabilization of these emulsions by embedding in the polymeric matrix wherein the small droplets of dispersed phase surrounded by surfactant molecules retains their identity and integrity. The said process steps include addition of o/w microemulsion to the highly viscous solution of film forming polymer, adjusting the fluidity to that required for casting a film if required, by adding additional water and drying the film under mild drying conditions such that a good film is formed but the immobilized micro-emulsion does not dry up to make the Active Pharmaceutical Ingredients of the microemulsion inactive. Mild drying conditions include, without limitation, drying at room temperature below 50° C., including at a temperature ranging from 25°-50° C., freeze drying etc. A polymeric gelling agent acts as gelling agent for stabilizing dispersed phase of microemulsion. In illustrative examples, HPMC (Hydroxypropyl Methyl Cellolose) have been used as a gelling agent. However, alternative polymeric gelling agents may also be used in place of HPMC, including, without limitation, acacia, alginic acid, bentonite, Carbopols® (now known as carbomers), carboxymethylcellulose. ethylcellulose, gelatin, hydroxyethylcellulose, hydroxypropyl cellulose, magnesium aluminum silicate (Veegum®), methylcellulose, poloxamers (Pluronics®), polyvinyl alcohol, sodium alginate, tragacanth, and xanthan gum. The resulting solution is dried at low temperature ranging from 25° to 40° to 50° C. or by freeze drying depending on the temperature sensitivity of the Active Pharmaceutical Ingredient added to the film. In the case of thermolabile Active Pharmaceutical Ingredients, the films are dried using freeze drying process. Surfactants may also be sued to keep the microemulsion dispersed in the film forming emulsion. Tween 80 is used in the illustration in this specification; but any other surfactant may be used, including, without limitation, benzalkonium chloride, benzethonium chloride, sodium or potassium oleate, triethanolamine stearate, sodium lauryl sulfate, sodium dioctyl sulfosuccinate, sodium docusate, sorbitan esters (Spans®), polyoxyethylene derivatives of sorbitan esters (Tweens®), glyceryl esters, labrasol, etc.

In one embodiment, the film dosage form incorporating microemulsion in liquid state is packed as Unit Dose in simple packaging means. The simple packaging means include, without limitations, a pouch packing or a strip packing. It may be appreciated here that incorporation of microemulsions in liquid form in a ready to use film, the competitive advantages of microemulsions over other dosage forms are retained. Shortcomings of vaccine delivery by oral route, for example polio vaccine which is in liquid state, get overcome when they are administered through other mucosal routes. Problems of the oral vaccines which are involved in storage, transportation, cool-chain and administration to a child without spillage during administration on account of the resistance of the child to drink it, regurgitation etc. can be overcome by incorporating the same in the film dosage form of this invention.

In a further embodiment of an orally dissolving thin film dosage form incorporating microemulsion in liquid state, bioavailability of protein and peptide drugs through oral route can potentially be increased by using suitable penetration enhancers in the microemulsion.

It is obvious that the packaging of the orally dissolving thin film dosage form incorporating microemulsion in liquid state does not need sophisticated packaging system as is required in the case of metered sprays etc.

The invention is illustrated by following non-limiting example. Any obvious variation or equivalent of it is considered and intended to be included in the scope of this disclosure. The below example shall make all other variations suggested above obvious to a person skilled in the art and can be achieved by routine experimentation.

Example 1

(a) Preparation of Plain w/o Microemulsion

| Ingredients | Parts in mg |
|---|---|
| Solution A | |
| Labrasol | 2.7 |
| Span 80 | 2.2 |
| Propylene glycol | 2 |
| Oil phase (Oleic acid) | 25 |
| Water | 4 |

Solution A was prepared by mixing Labrasol, Span 80 and Propylene glycol and to this Oleic acid was added.

1. Water was then added to the mixture prepared in step 1 to form w/o microemuision. The droplet size as measured by Horiba Nanoparticle analyzer was 26.12±2.9 nm.

(b) Preparation of Plain w/o Microemulsion Loaded Film

| Ingredients | Amount (g) |
|---|---|
| HPMC | 40 |
| Tween 80 | 1.5 |
| Plain w/o Microemulsion according to Example 1 (a) | 40 |
| Water | 3 |

Procedure

1. HPMC, 40 g, was dispersed in 100 ml of water to make a solution with consistency sufficient to cast a film and stirred to form solution.

2. To this then accurately weighed quantity of Tween 80, and w/o microemulsion prepared in (a) was added.

3. This resulting double emulsion mixture was mixed properly and casted with the help of SS scraper to the desired thickness.

4. The film was then allowed to dry at room temperature. The film when stirred in water gets dissolved in less than 30 seconds. The size of all the particles obtained after dissolving film in water was found to be in the range of 5 nm to 250 nm.

Example 2

(a) Preparation of w/o Microemulsion of Insulin

Insulin loaded water-in-oil (w/o) microemulsion of Insulin was prepared by mixing Insulin, Span 80 and propylene glycol in 2.7, 2.2 and 2 grams respectively. This is then added to 25 g of oleic acid. To this mixture 4.0 g of water is added slowly.

Particle size of Insulin Loaded w/o emulsion had particles of size in the range of 52 nm to 83 nm.

(b) Preparation of w/o (Water-in-Oil) Microemulsion Loaded Sub-Lingual Films of Insulin

| Ingredients | Quantity in gram |
|---|---|
| HPMC | 28 |
| PVA | 7 |
| PEG 1000 | 1.5 |
| Tween 80 | 1.5 |
| Neusilin | 7 |
| Insulin loaded w/o Microemulsion according to Example 2(a) described above | 45 |
| Water | 100 |

An orally dissolving thin film dosage form incorporating microemulsion in liquid state containing w/o microemulsion of insulin was made by using following steps:

A dispersion was prepared by dissolving HPMC and PVA 100 ml of water to make a solution with viscosity sufficient to cast a film. To this dispersion PEG 1000, Tween 80 and neusilin was added and mixed completely. This dispersion was allowed to stand for four hours.

Insulin loaded microemulsion, 45 g, made as per Example 2(a) was added to polymer dispersion.

Resulting double emulsion was casted in the form films with 250 microns as wet film thickness.

These films were then dried with the help of freeze dryer to the desired level of moisture content.

The films were found to be flexible, non tacky and dissolved in water in less than 30 seconds. After dissolution, the water contained particles of size ranging between 250 nm to 1250 nm.

Example 3

Efficacy of Insulin Administered as Microemulsion Though Sub-Lingual Film

The Insulin loaded sub-lingual films of Example 2 were administered to four diabetic human volunteers by sublingual route at fasting stage and this stage was maintained during the study period. Each film contained dose of insulin equivalent to 25 IU. and blood glucose levels were measured at 0, 1 and 2 hours. Reduction in blood glucose levels was observed in the range of 46±4 mg/dl.

| Volunteer | Blood Glucose levels in mg/dl | | | Reduction in blood glucose level in mg/dl |
|---|---|---|---|---|
| | Initial | 60 minutes | 120 minutes | |
| 1 | 140 | 123 | 94 | 46 |
| 2 | 152 | 127 | 102 | 50 |
| 3 | 137 | 114 | 88 | 49 |
| 4 | 132 | 119 | 91 | 41 |

Example 4

Preparation of Film Dosage Form Containing no Microemulsion and Size of Particles After Dissolution in Water

| Ingredients | Amount in (g) |
|---|---|
| HPMC | 40 |
| PVA | 10 |
| Sucralose | 2.5 |
| Water | 100 |

Procedure

1. First the polymer HPMC was dispersed in 50 g of water and mixed.
2. PVA was dissolved in 50 g of water separately and was mixed with HPMC solution.
3. To this solution prepared in step 2, accurately weighed quantity of sucralose was added.
4. This mixture was mixed properly with the help of a glass rod and then the films were casted on a support with the help of SS scraper to the desired thickness.
5. This film was then allowed to dry at 60° C.
6. These films when dispersed in water resulted in clear solution and no particles were detected when measured using particle size analyzer.

Example 5

Preparation of o/w Microemulsion of Haloperidol

Procedure

| Ingredients | Amount in Percent w/v |
|---|---|
| Tween 80 | 28.57 |
| Isopropyl alcohol | 28.57 |
| Saturated solution of haloperidol in Oleic acid | 14.29 |
| Water | 28.57 |

1. Tween 80 and isopropyl alcohol were mixed to obtain a homogenous solution (Solution A).
2. Saturated solution of haloperidol was prepared in oleic acid (Solution B).
3. Solution B was added to solution A and mixed. To this mixture required quantity of water was added and o/w microemulsion was ready in the form of clear transparent liquid. The droplet size as measured by Horiba Nanoparticle analyzer was 31.45±1.7 nm.

Example 6

Preparation of o/w Microemulsion Loaded Film of Haloperidol

| Components | Amount in percent |
|---|---|
| HPMC | 39.02 |
| PVA | 9.75 |
| o/w Microemulsion | 48.78 |
| Sucralose | 2.43 |

Procedure

1. Accurately weighed quantities of HPMC, PVA, sucralose and o/w microemulsion were mixed properly with the help of a stirrer and then the films were casted on a support with the help of SS scraper to the desired thickness.
2. This film was then allowed to dry at room temperature.
3. The films were found to have folding endurance value of 20 to 25.
4. The film when stirred in water gets dissolved in less than 30 seconds.
5. The size of all the particles obtained after dissolving film in water was found to be in the range of 50 nm to 500 nm.

The invention claimed is:

1. A ready to use film dosage form comprising:
a microemulsion of an Active Pharmaceutical Ingredient embedded in a thin polymeric film matrix,
wherein
the embedded microemulsion is in its original state with moisture trapped in it;
the original state of the microemulsion being a liquid state, and
the microemulsion being one that is formed spontaneously on mixing all the components.

2. The ready to use film dosage form of claim 1 wherein the thin polymeric matrix is water soluble.

3. The ready to use film dosage form of claim 1 wherein the microemulsion is a double microemulsion.

4. The ready to use film dosage form of claim 2 wherein the moisture content of the film is at least equal to the moisture bound in the emulsion component.

5. The film dosage form according to claim 1 wherein micro-emulsion of an Active Pharmaceutical Ingredient that is capable of being absorbed through mucosal route and added in a therapeutically effective quantity.

6. The film dosage form according to claim 1 containing microemulsion, wherein the microemulsion is a water-in-oil (w/o) microemulsion or an oil-in-water microemulsion.

7. The film dosage form according to claim 1 wherein the active ingredient that is capable of being absorbed through mucosal route comprises macromolecules that degrade in gastrointestinal tract or have poor permeability through the biological membranes.

8. The film dosage form according to claim 7 wherein the macromolecule that degrades in gastrointestinal tract is one or more selected from the group consisting of insulin, teriperatide, calcitonin, glucagon, somatostatin, leptin, erythropoietin and antibodies.

9. The film dosage form according to claim 7 further containing a macromolecule penetration/absorption enhancer.

10. The film dosage form according to claim 6 wherein the oil-in-water micro-emulsion is made of a poorly water soluble active ingredient added in a therapeutically effective quantity.

11. The film dosage form according to claim 10 wherein the poorly water soluble active ingredient is selected, one or more, from the group of drugs consisting of Haloperidol, aceclofenac, meloxicam, etoricoxib, fenofibrate, itraconazole, tacrolimus, cyclosporine A, glimipiride, gliclazide, carvedilol, fexofenadine, and zolpidem.

12. The film dosage form according to claim 1 wherein the film is bioadhesive, enabling administration of drugs through mucosal route.

13. The film dosage form according to claim 12 wherein the mucosal route is one or more selected from the group buccal, sublingual, nasal, rectal and vaginal route.

14. The film dosage form according to claim 1 wherein upon dissolution/dispersion the film produces micro-emulsion.

15. The ready to use film dosage form of claim 3 wherein the moisture content of the film is at least equal to the moisture bound in the emulsion component.

16. A process of making ready to use film dosage form comprising a microemulsion of an Active Pharmaceutical Ingredient embedded in a thin polymeric matrix film in its original state retaining the moisture trapped in the microemulsion embedded in the polymeric film, the original state of the microemulsion being a liquid state and the microemulsion being one that is formed spontaneously on mixing all the components; the process comprising steps of:

forming a film forming dispersion by addition of oil-in-water microemulsion of active pharmaceutical ingredient and excipients to highly viscous solution of film forming polymer, adjusting the fluidity to that required for casting a film if required, casting the same in the form of a film and drying of the cast of the film being carried out by means of drying conditions that are selected to achieve drying of the film retaining the moisture trapped in the microemulsion embedded in the polymeric film.

17. The process of making ready to use film dosage form according to claim 16 wherein the drying condition is selected from the group consisting of (a) use of mild heat for thermostable drugs, and (b) carrying out (i) film casting and drying without the need of heat, or (ii) freeze drying for thermolabile drugs.

18. The process of claim 16 wherein the microemulsion is selected from the group consisting of oil-in-water emulsion, or water-in-oil microemulsion, or double microemulsion.

19. The process of claim 16 wherein the micro-emulsion in the film forming emulsion is subjected to gelation/gelling upon removal of water during drying.

* * * * *